US012569221B2

(12) United States Patent
Misener

(10) Patent No.: US 12,569,221 B2
(45) Date of Patent: Mar. 10, 2026

(54) SYSTEMS AND METHODS FOR INFRARED-ENHANCED ULTRASOUND VISUALIZATION

(71) Applicant: Bard Access Systems, Inc., Salt Lake City, UT (US)

(72) Inventor: Anthony K. Misener, Bountiful, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 194 days.

(21) Appl. No.: 16/548,607

(22) Filed: Aug. 22, 2019

(65) Prior Publication Data

US 2020/0060643 A1   Feb. 27, 2020

Related U.S. Application Data

(60) Provisional application No. 62/721,358, filed on Aug. 22, 2018.

(51) Int. Cl.
*A61B 8/08* (2006.01)
*A61B 1/07* (2006.01)
*A61B 5/00* (2006.01)

(52) U.S. Cl.
CPC .............. *A61B 8/0841* (2013.01); *A61B 1/07* (2013.01); *A61B 5/0035* (2013.01); *A61B 5/0075* (2013.01)

(58) Field of Classification Search
CPC ..... A61B 8/0841; A61B 8/467; A61B 8/0891; A61B 8/463; A61B 8/4444; A61B 8/4416; A61B 5/0086; A61B 5/0035; A61B 5/0075; A61B 1/07
See application file for complete search history.

(56) References Cited

U.S. PATENT DOCUMENTS

| | | | |
|---|---|---|---|
| 5,099,845 | A | 3/1992 | Besz et al. |
| 5,211,165 | A | 5/1993 | Dumoulin et al. |
| 5,423,321 | A | 6/1995 | Fontenot |
| 5,517,997 | A | 5/1996 | Fontenot |
| 5,622,170 | A | 4/1997 | Schulz |

(Continued)

FOREIGN PATENT DOCUMENTS

| | | |
|---|---|---|
| WO | 99/64099 A1 | 12/1999 |
| WO | 2015074045 A2 | 5/2015 |

OTHER PUBLICATIONS

Chen, "Image Guided Robotics for Autonomous Venipuncture", Rutgers University, pp. 1-256 (Year: 2016).*

(Continued)

*Primary Examiner* — Adil Partap S Virk
(74) *Attorney, Agent, or Firm* — Rutan & Tucker LLP

(57) ABSTRACT

A system and method for providing enhanced ultrasound images for accessing a vasculature of a patient is disclosed. The system includes an ultrasound imaging device including a probe with a light detector disposed at a distal end thereof. A medical device includes an infrared emitter disposed a distal tip thereof. The emitter provides infrared light that illuminates surrounding tissue. Reflected light is detected and interpreted based on the profile of absorbance spectra which can be used to identify different tissue structures. This light-based information is superimposed on an ultrasound image of the vessel to facilitate first-stick access of patient vasculature.

11 Claims, 8 Drawing Sheets

(56) References Cited

U.S. PATENT DOCUMENTS

| 5,879,306 A | 3/1999 | Fontenot et al. |
| 5,906,579 A | 5/1999 | Vander Salm et al. |
| 6,081,741 A | 6/2000 | Hollis |
| 6,178,346 B1 | 1/2001 | Amundson et al. |
| 6,208,887 B1 | 3/2001 | Clarke |
| 6,343,227 B1 | 1/2002 | Crowley |
| 6,593,884 B1 | 7/2003 | Gilboa et al. |
| 6,597,941 B2 | 7/2003 | Fontenot et al. |
| 6,650,923 B1 | 11/2003 | Lesh et al. |
| 6,685,666 B1 | 2/2004 | Fontenot |
| 6,690,958 B1* | 2/2004 | Walker ............... A61B 5/14542 |
| | | 600/309 |
| 6,690,966 B1 | 2/2004 | Rava et al. |
| 6,701,181 B2 | 3/2004 | Tang et al. |
| 6,711,426 B2 | 3/2004 | Benaron et al. |
| 6,816,743 B2 | 11/2004 | Moreno et al. |
| 6,892,090 B2 | 5/2005 | Verard et al. |
| 6,895,267 B2 | 5/2005 | Panescu et al. |
| 7,132,645 B2 | 11/2006 | Kom |
| 7,273,056 B2 | 9/2007 | Wilson et al. |
| 7,366,562 B2 | 4/2008 | Dukesherer et al. |
| 7,366,563 B2 | 4/2008 | Kleen et al. |
| 7,396,354 B2 | 7/2008 | Rychnovsky et al. |
| 7,406,346 B2 | 7/2008 | Kleen et al. |
| 7,515,265 B2 | 4/2009 | Alfano et al. |
| 7,532,920 B1 | 5/2009 | Ainsworth et al. |
| 7,587,236 B2 | 9/2009 | Demos et al. |
| 7,603,166 B2 | 10/2009 | Casscells et al. |
| 7,729,735 B1 | 6/2010 | Burchman |
| 7,757,695 B2 | 7/2010 | Wilson et al. |
| 7,758,499 B2 | 7/2010 | Adler |
| 7,840,253 B2 | 11/2010 | Tremblay et al. |
| 7,992,573 B2 | 8/2011 | Wilson et al. |
| 8,032,200 B2 | 10/2011 | Tearney et al. |
| 8,060,187 B2 | 11/2011 | Marshik-Geurts et al. |
| 8,073,517 B1 | 12/2011 | Burchman |
| 8,078,261 B2 | 12/2011 | Imam |
| 8,187,189 B2 | 5/2012 | Jung et al. |
| 8,267,932 B2 | 9/2012 | Baxter et al. |
| 8,369,932 B2 | 2/2013 | Cinbis et al. |
| 8,571,640 B2 | 10/2013 | Holman |
| 8,798,721 B2 | 8/2014 | Dib |
| 8,954,134 B2 | 2/2015 | Imam |
| 2002/0198457 A1 | 12/2002 | Tearney et al. |
| 2003/0092995 A1 | 5/2003 | Thompson |
| 2004/0215072 A1 | 10/2004 | Zhu |
| 2006/0036164 A1* | 2/2006 | Wilson ..................... A61B 5/06 |
| | | 600/424 |
| 2006/0241395 A1 | 10/2006 | Kruger et al. |
| 2006/0241492 A1 | 10/2006 | Boese et al. |
| 2007/0225553 A1 | 9/2007 | Shahidi |
| 2007/0299425 A1 | 12/2007 | Waner et al. |
| 2008/0058638 A1* | 3/2008 | Zhu ..................... A61B 5/4312 |
| | | 600/425 |
| 2008/0146874 A1* | 6/2008 | Chen ................... A61B 1/0676 |
| | | 600/109 |
| 2008/0172119 A1 | 7/2008 | Yamasaki et al. |
| 2009/0264768 A1* | 10/2009 | Courtney ............. A61B 5/0066 |
| | | 600/463 |
| 2010/0016729 A1* | 1/2010 | Futrell ................. A61B 5/0086 |
| | | 600/473 |
| 2010/0056928 A1* | 3/2010 | Zuzak .................. A61B 5/0071 |
| | | 600/476 |
| 2011/0166442 A1* | 7/2011 | Sarvazyan ............. A61B 34/20 |
| | | 600/424 |
| 2011/0245659 A1* | 10/2011 | Ma ......................... A61B 5/066 |
| | | 600/424 |
| 2011/0245662 A1 | 10/2011 | Eggers et al. |
| 2011/0282188 A1* | 11/2011 | Burnside ................ A61B 90/98 |
| | | 600/424 |
| 2011/0295108 A1* | 12/2011 | Cox ....................... A61B 5/339 |
| | | 600/424 |
| 2012/0123205 A1* | 5/2012 | Nie ....................... A61B 5/0075 |
| | | 600/109 |
| 2012/0143029 A1* | 6/2012 | Silverstein ........... A61B 8/0891 |
| | | 600/374 |
| 2012/0184827 A1 | 7/2012 | Shwartz et al. |
| 2012/0184955 A1 | 7/2012 | Pivotto et al. |
| 2012/0209359 A1 | 8/2012 | Chen et al. |
| 2013/0211246 A1 | 8/2013 | Parasher |
| 2013/0218024 A1* | 8/2013 | Boctor ................... A61B 46/00 |
| | | 600/476 |
| 2013/0310668 A1 | 11/2013 | Young |
| 2014/0121468 A1 | 5/2014 | Eichenholz |
| 2014/0221829 A1 | 8/2014 | Maitland et al. |
| 2015/0031987 A1 | 1/2015 | Pameijer et al. |
| 2015/0080688 A1 | 3/2015 | Cinbis et al. |
| 2015/0080763 A1 | 3/2015 | Bonutti |
| 2015/0099979 A1 | 4/2015 | Caves et al. |
| 2015/0119700 A1 | 4/2015 | Liang et al. |
| 2015/0209113 A1 | 7/2015 | Burkholz et al. |
| 2015/0257735 A1* | 9/2015 | Ball ........................ A61B 8/462 |
| | | 600/443 |
| 2015/0327836 A1 | 11/2015 | Stone et al. |
| 2016/0008057 A1* | 1/2016 | Peppou .................. A61B 18/02 |
| | | 600/478 |
| 2016/0038119 A1* | 2/2016 | Desjardins ........... A61B 8/4444 |
| | | 600/424 |
| 2016/0213293 A1* | 7/2016 | Beute .................... A61B 5/0075 |
| 2016/0256101 A1* | 9/2016 | Aharoni .............. A61B 5/0086 |
| 2016/0270662 A1* | 9/2016 | Takayama ............ A61B 5/0075 |
| 2017/0224420 A1* | 8/2017 | Stringer ................ A61B 34/20 |
| 2018/0008243 A1* | 1/2018 | Irisawa .................. G01N 29/22 |
| 2018/0078239 A1* | 3/2018 | Ball ...................... A61B 5/7445 |
| 2018/0116630 A1* | 5/2018 | Dykes .................. A61B 8/4483 |
| 2018/0161502 A1* | 6/2018 | Nanan ...................... A61B 5/15 |
| 2018/0221566 A1 | 8/2018 | Ohnmacht et al. |
| 2018/0344228 A1* | 12/2018 | Yelin .................. A61B 5/14535 |
| 2019/0056693 A1* | 2/2019 | Gelman .............. G03H 1/0005 |

OTHER PUBLICATIONS

PCT/US2019/047756 filed Aug. 22, 2019 International Search Report and Written Opinion dated Nov. 15, 2019.

EP19852441.5 filed Mar. 18, 2021 Extended European Search Report dated Apr. 13, 2022.

PCT/US2019/047756 filed Aug. 22, 2019 International Preliminary Report on Patentability dated Feb. 23, 2021.

* cited by examiner

SYSTEMS AND METHODS FOR INFRARED-ENHANCED ULTRASOUND VISUALIZATION

PRIORITY

This application claims the benefit of priority to U.S. Provisional Application No. 62/721,358, filed Aug. 22, 2018, titled, "Systems And Methods For Infrared-Enhanced Ultrasound Visualization," which is incorporated by reference in its entirety into this application.

BRIEF SUMMARY

Accessing the patients vasculature is a common technique, but also one that continues to be problematic and require the use and loss of multiple needles or catheters in failed cannulation attempts. Ultrasound has become prevalent as a tool to improve first stick success through visualization of vessel size, depth and location. However, visualizing the needle crossing into the vessel and staying in the vessel can still be difficult under ultrasound guidance.

Briefly summarized, a system and method for providing enhanced ultrasound images for accessing a vasculature of a patient is disclosed. The system includes an ultrasound imaging device including a probe with a light detector disposed at a distal end thereof. A medical device includes an infrared emitter disposed a distal tip thereof. The emitter provides light in the wavelength ranges of infrared, or near-infrared, which is capable of penetrating biological tissue to a greater extent than other wavelengths. Further, different tissue components, such as oxyhemoglobin, deoxyhemoglobin, water, melanin, fat, etc., absorb certain wavelengths of infrared light more readily than others, providing differing spectra of absorption coefficients. Accordingly, detecting and interpreting these absorption coefficients can provide information regarding the tissue type and therefore location of the emitter. This light-based information can be superimposed on an ultrasound image of the vessel to facilitate first-stick access of patient vasculature.

Disclosed herein is an imaging system for guiding a medical device within a body of a patient, comprising, an ultrasound probe for producing and receiving ultrasound signals, an emitter configured for emitting an infrared light, the emitter coupled to a distal tip of the medical device, a detector configured to detect the infrared light emitted from the emitter, and a display configured to provide an enhanced ultrasound image including ultrasound information from the ultrasound probe and light-based information from the detector.

In some embodiments, the emitter is configured to emit light within a range of wavelengths between 780 nm and 3000 nm. The emitter further includes a light source capable of producing an infrared light. The system further includes a light source, capable of producing an infrared light and positioned distally of the emitter, and a fiber optic cable extending from the light source to the emitter that communicates light therebetween. The detector is included with a distal end of the probe. The light-based information from the detector includes an image of an illuminated portion of the patient. The light-based information from the detector includes detecting and interpreting the absorption spectra of reflected light to determine a type of tissue structure that the emitter is illuminating. The detector determines a reflected light from the emitter is red-shifted and indicates that a vessel being accessed is arterial. The detector determines a reflected light from the emitter is blue-shifted and indicates that a vessel being accessed is venous. The emitter is included with a distal end of a stylet, disposed within a lumen of the medical device. The medical device includes one of a needle and a catheter.

Also disclosed herein is a method of accessing a vasculature of a patient, the method comprising, providing an ultrasound probe including a light detector disposed at a distal end thereof and a medical device for accessing the vasculature of the patient, placing an ultrasound probe adjacent a skin surface of the patient, the ultrasound probe including a light detector to detect a vessel, inserting a medical device through the skin surface of the patient, the medical device including an emitter at a distal tip thereof, illuminating subcutaneous tissue above the vessel with infrared light of the emitter to indicate a location of the vessel, advancing the tip of the medical device into the vessel and illuminating an inner portion of the vessel to indicate the distal tip of the medical device being in the vessel, and providing an enhanced ultrasound image, including light-based images, to indicate to a user a position of the tip of the medical device relative to the vessel.

In some embodiments, the method further includes advancing the distal tip through a far side of the vessel to illuminate a subcutaneous tissue below the vessel. The emitter provides light within a wavelength range of between 780 nm and 3000 nm. The light detector determines a reflected light from the emitter is red-shifted and provides an enhanced ultrasound image indicating the vessel is arterial. The light detector determines a reflected light from the emitter is blue-shifted and provides an enhanced ultrasound image indicating the vessel is venous. The emitter is included with distal tip of a stylet, disposed within a lumen of the medical device. The medical device includes one of a needle and a catheter.

BRIEF DESCRIPTION OF THE DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which.

DETAILED DESCRIPTION OF SELECTED EMBODIMENTS

Figures 1, 2:
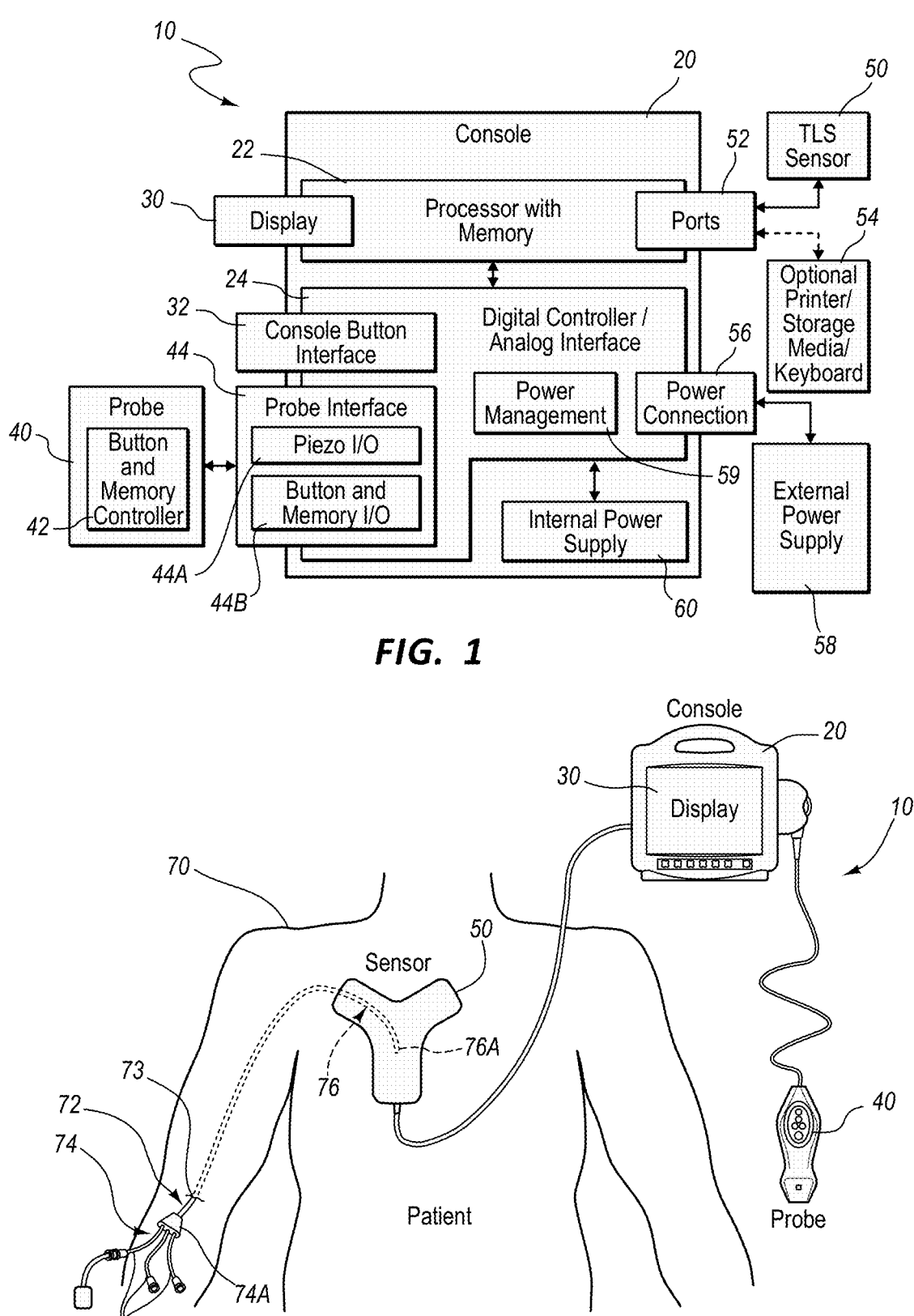
FIG. 1 is a block diagram depicting various elements of an integrated system for intravascular placement of a catheter, according to embodiments disclosed herein.
FIG. 2 is a simplified view of a patient, and a catheter being inserted therein, with assistance of the integrated system of FIG. 1.

Reference will now be made to figures wherein like structures will be provided with like reference designations. It is understood that the drawings are diagrammatic and schematic representations of exemplary embodiments of the present invention, and are neither limiting nor necessarily drawn to scale.

For clarity it is to be understood that the word "proximal" refers to a direction relatively closer to a clinician using the device to be described herein, while the word "distal" refers to a direction relatively further from the clinician. For example, the end of a catheter placed within the body of a patient is considered a distal end of the catheter, while the catheter end remaining outside the body is a proximal end of the catheter. Also, the words "including," "has," and "having," as used herein, including the claims, shall have the same meaning as the word "comprising."

Embodiments of the present invention are generally directed to systems and methods for providing enhanced ultrasound images produced by an ultrasound imaging device including an ultrasound probe, such as the system described herein. The enhanced image is provided by a light source that provides additional subcutaneous visualization for incorporation into the ultrasound image. In an embodiment, the light source emits light in the infrared and/or near-infrared wavelength range, although other wavelengths are contemplated. As used herein, the infrared range of wavelengths are between about 700 nm to about 1 mm, the near-infrared range wavelengths are between about 780 nm and about 3000 nm. A detector is coupled with the ultrasound probe to detect the light emitted from the light source to enable the system to combine the ultrasound and light-based images and produce an enhanced image to the clinician. The enhanced image in turn assists the clinician to determine with relatively greater accuracy the position of a distal end of a catheter, needle, or similar device that is being inserted into a vessel or other subcutaneous portion of the body of a patient.

The accompanying figures depict various features of embodiments of a catheter placement system configured for accurately placing a catheter within the vasculature of a patient. While embodiments disclosed herein are directed to catheter placement, it will be appreciated that the systems and methods can also be used with different types of catheters, such as peripherally-inserted central catheter ("PICC"), central venous catheter ("CVC"), and the like, needles, stylets, guidewires, introducers, trocars, or the like, or combinations thereof. In an embodiment, the catheter placement system employs at least two modalities for improving catheter placement accuracy: 1) ultrasound-assisted guidance for introducing the catheter into the patient's vasculature; and 2) a tip location/navigation system ("TLS"), or magnetically-based tracking of the catheter tip during its advancement through the tortuous vasculature path to detect and facilitate correction of any tip malposition during such advancement. The ultrasound guidance and tip location features of the present system according to one embodiment are integrated into a single device for use by a clinician placing the catheter. Integration of these two modalities into a single device simplifies the catheter placement process and results in relatively faster catheter placements. For instance, the integrated catheter placement system enables ultrasound and TLS activities to be viewed from a single display of the integrated system. Also, controls located on an ultrasound probe of the integrated device, which probe is maintained within the sterile field of the patient during catheter placement, can be used to control functionality of the system, thus precluding the need for a clinician to reach out of the sterile field in order to control the system.

In an embodiment, a third modality, for example ECG signal-based catheter tip guidance, is included in the integrated system to enable guidance of the catheter tip to a desired position with respect to a node of the patient's heart from which the ECG signals originate. Such ECG-based positional assistance is also referred to herein as "tip confirmation."

Combination of the three modalities above, according to an embodiment, enables the catheter placement system to facilitate catheter placement within the patient's vasculature with a relatively high level of accuracy, i.e., placement of the distal tip of the catheter in a predetermined and desired position. Moreover, because of the ECG-based guidance of the catheter tip, correct tip placement may be confirmed without the need for a confirmatory X-ray. This, in turn, reduces the patient's exposure to potentially harmful x-rays, the cost and time involved in transporting the patient to and from the x-ray department, costly and inconvenient catheter repositioning procedures, etc.

So configured, the catheter placement system serves as one exemplary environment in which embodiments of enhanced subcutaneous imaging using ultrasound imaging with infrared can be practiced. Further details of the catheter placement system can be found, for example, in U.S. Pat. Nos. 8,388,541; 8,781,555; 8,849,382; 9,456,766; 9,492, 097; 9,521,961; 9,554,716; 9,636,031; 9,649,048; U.S. Publication No. 2014/0031674; U.S. Publication No. 2014/ 0046261; and U.S. Publication No. 2014/0188133, each of which is incorporated by reference in its entirety into this application.

Reference is first made to FIGS. 1 and 2 which depict various components of a catheter placement system ("system"), generally designated at 10, configured in accordance with an embodiment and providing an example environment in which embodiments of the enhanced subcutaneous imaging using ultrasound and infrared, can be practiced. It will be appreciated that the embodiments described herein can be practiced in connection with other ultrasound imaging systems, catheter placement systems, and the like, in addition to those described herein. As such, the following discussion is not intended to be limiting.

As shown in FIGS. 1 and 2, the system 10 generally includes a console 20, display 30, probe 40, and sensor 50, each of which is described in further detail herein. FIG. 2 shows the general relation of these components to a patient 70 during a procedure to place a catheter 72 into the patient vasculature through a skin insertion site 73. FIG. 2 shows that the catheter 72 generally includes a proximal portion 74 that remains exterior to the patient and a distal portion 76 that resides within the patient vasculature after placement is complete. The system 10 is employed to ultimately position a distal tip 76A of the catheter 72 in a desired position within the patient vasculature. In an embodiment, the desired position for the catheter distal tip 76A is proximate the patient's heart, such as in the lower one-third ($\frac{1}{3}^{rd}$) portion of the Superior Vena Cava ("SVC"). Of course, the system 10 can be employed to place the catheter distal tip in other locations. The catheter proximal portion 74 further includes a hub 74A that provides fluid communication between the one or more lumens of the catheter 72 and one or more extension legs 74B extending proximally from the hub.

An example implementation of the console 20 is shown in FIG. 1, though it is appreciated that the console can take one of a variety of forms. A processor 22, including non-volatile memory such as EEPROM for instance, is included in the console 20 for controlling system function during operation of the system 10, thus acting as a control processor. A digital controller/analog interface 24 is also included with the console 20 and is in communication with both the processor 22 and other system components to govern interfacing between the probe 40, sensor 50, and other system components.

The system 10 further includes ports 52 for connection with the sensor 50 and optional components 54 including a printer, storage media, keyboard, etc. The ports in one embodiment are USB ports, though other port types or a combination of port types can be used for this and the other interfaces connections described herein. A power connection 56 is included with the console 20 to enable operable connection to an external power supply 58. An internal power supply 60, such as a battery, can also be employed, either with or exclusive of an external power supply. Power management circuitry 59 is included with the digital controller/analog interface 24 of the console to regulate power use and distribution.

The display 30 in the present embodiment is integrated into the console 20 and is used to display information to the clinician during the catheter placement procedure. In another embodiment, the display may be separate from the console. As will be seen, the content depicted by the display 30 changes according to which mode the catheter placement system is in: US, TLS, or in other embodiments, ECG tip confirmation. In one embodiment, a console button interface 32 (see FIG. 1) and buttons included on the probe 40 can be used to immediately call up a desired mode to the display 30 by the clinician to assist in the placement procedure. In one embodiment, information from multiple modes, such as TLS and ECG, may be displayed simultaneously, such as in FIG. 4B. Thus, the single display 30 of the system console 20 can be employed for ultrasound guidance in accessing a patient's vasculature, TLS guidance during catheter advancement through the vasculature, and ECG-based confirmation of catheter distal tip placement with respect to a node of the patient's heart. In an embodiment, the display 30 is an LCD, touchscreen display, or similar device.

Figure 3A:
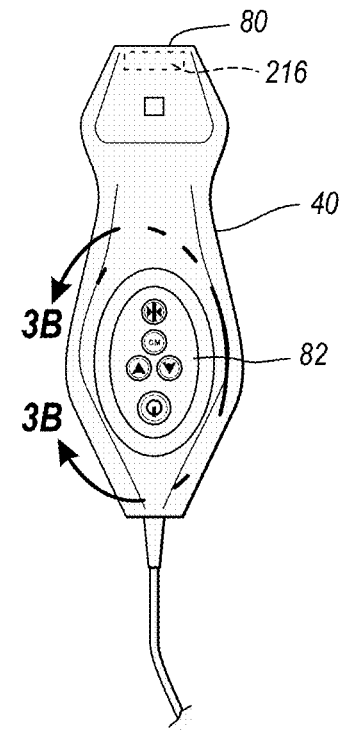
FIGS. 3A and 3B are views of a probe of the integrated system of FIG. 1.
Figure 3B:
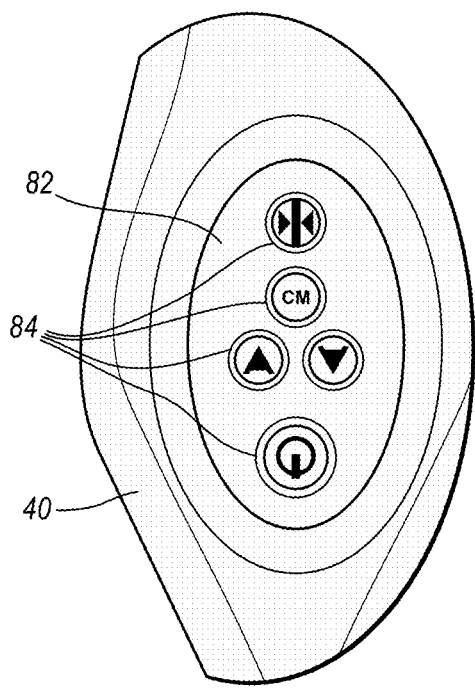

FIGS. 3A and 3B depict features of the probe 40 according to an embodiment. The probe 40 is employed in connection with the first modality disclosed herein, i.e., ultrasound ("US")-based visualization of a vessel, such as a vein, in preparation for insertion of the catheter 72 into the vasculature. Such visualization gives real time ultrasound guidance for introducing the catheter into the vasculature of the patient and assists in reducing complications typically associated with such introduction, including inadvertent arterial puncture, hematoma, pneumothorax, and the like.

The handheld probe 40 includes a head 80 that houses a piezoelectric array for producing ultrasonic pulses and for receiving echoes thereof after reflection by the patient's body when the head is placed against the patient's skin proximate the prospective insertion site 73 (FIG. 2). The probe 40 further includes a plurality of control buttons 84, which can be included on a button pad 82. In an embodiment, the modality of the system 10 can be controlled by the control buttons 84, thus eliminating the need for the clinician to reach out of the sterile field, which is established about the patient insertion site prior to catheter placement, to change modes via use of the console button interface 32. In an embodiment, control buttons 84 can also be located on a touchscreen display 30, as shown in FIG. 4B.

As such, in an embodiment a clinician employs the first (US) modality to determine a suitable insertion site and establish vascular access, such as with a needle or introducer, then with the catheter. The clinician can then seamlessly switch, via button pushes on the probe button pad 82, to the second (TLS) modality without having to reach out of the sterile field. The TLS mode can then be used to assist in advancement of the catheter 72 through the vasculature toward an intended destination.

FIG. 1 shows that the probe 40 further includes button and memory controller 42 for governing button and probe operation. The button and memory controller 42 can include non-volatile memory, such as EEPROM, in an embodiment. The button and memory controller 42 is in operable communication with a probe interface 44 of the console 20, which includes a piezo input/output component 44A for interfacing with the probe piezoelectric array and a button and memory input/output component 44B for interfacing with the button and memory controller 42.

Figure 4A:
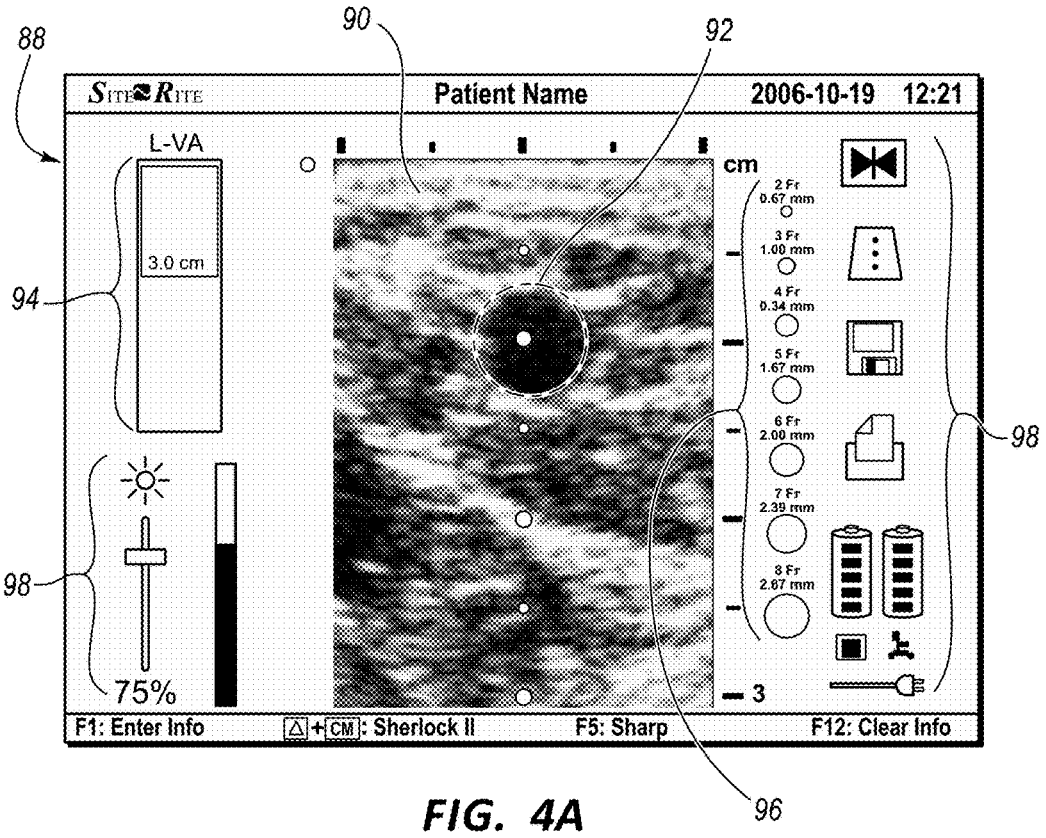
FIG. 4A is a screenshot of an ultrasound image as depicted on a display of the integrated system of FIG. 1.
Figure 4B:
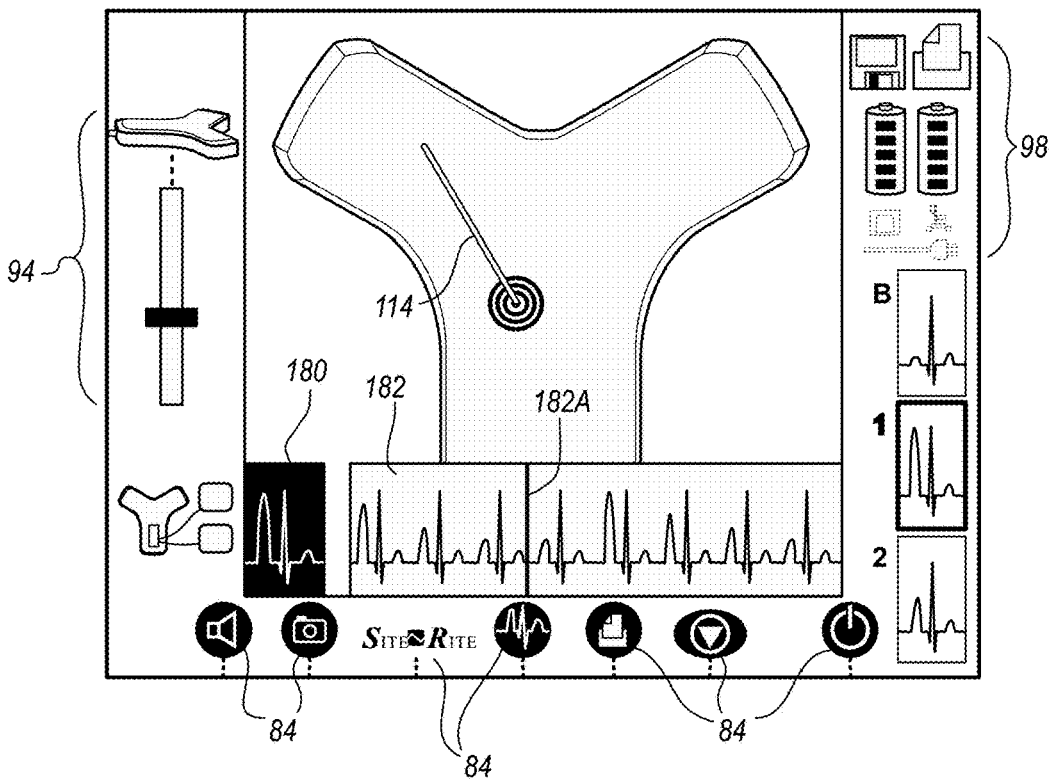
FIG. 4B is a screenshot of a multimodal image as depicted on a display of the integrated system of FIG. 1.

FIG. 4A shows an example screenshot 88 as depicted on the display 30 while the system 10 is in its first ultrasound modality. An image 90 of a subcutaneous region of the patient 70 is shown, depicting a cross section of a vein 92. The image 90 is produced by operation of the piezoelectric array of the probe 40. Also included on the display screenshot 88 is a depth scale indicator 94, providing information regarding the depth of the image 90 below the patient's skin, a lumen size scale 96 that provides information as to the size of the vein 92 relative to standard catheter lumen sizes, and other indicia 98 that provide information regarding status of the system 10 or possible actions to be taken, e.g., freeze frame, image templates, data save, image print, power status, image brightness, etc.

Note that while a vein is depicted in the image 90, other body lumens or portions can be imaged in other embodiments. Note that the US mode shown in FIG. 4A can be simultaneously depicted on the display 30 with other modes, such as the TLS mode, if desired, e.g. FIG. 4B. In addition to the visual display 30, aural information, such as beeps, tones, etc., can also be employed by the system 10 to assist the clinician during catheter placement. Moreover, the buttons included on the probe 40 and the console button interface 32, 84 can be configured in a variety of ways, including the use of user input controls in addition to buttons, such as slide switches, toggle switches, electronic or touch-sensitive pads, etc. Additionally, both US and TLS activities can occur simultaneously or exclusively during use of the system 10.

As just described, the handheld ultrasound probe 40 is employed as part of the integrated catheter placement system 10 to enable US visualization of the peripheral vasculature of a patient in preparation for transcutaneous introduction of the catheter. In the present example embodiment, however, the probe is also employed to control functionality of the TLS portion, or second modality, of the system 10 when navigating the catheter toward its desired destination within the vasculature as described below. Again, as the probe 40 is used within the sterile field of the patient, this feature enables TLS functionality to be controlled entirely from within the sterile field. Thus the probe 40 is a dualpurpose device, enabling convenient control of both US and TLS functionality of the system 10 from the sterile field. In an embodiment, the probe can also be employed to control some or all ECG-related functionality, or third modality, of the catheter placement system 10, as described herein.

The catheter placement system 10 further includes the second modality described herein, i.e., the magnetically-based catheter TLS, or tip location system. The TLS enables the clinician to quickly locate and confirm the position and/or orientation of the catheter 72, such as a peripherally-inserted central catheter ("PICC"), central venous catheter ("CVC"), or other suitable catheter, during initial placement into and advancement through the vasculature of the patient 70. Specifically, the TLS modality detects a magnetic field generated by a magnetic element-equipped tip location stylet, which is pre-loaded in one embodiment into a longitudinally defined lumen of the catheter 72, thus enabling the clinician to ascertain the general location and orientation of the catheter tip within the patient body. In one embodiment, the magnetic assembly can be tracked using the teachings of one or more of the following U.S. Pat. Nos. 5,775,322; 5,879,297; 6,129,668; 6,216,028; and 6,263,230, the contents of which are incorporated herein by reference in their entireties. The TLS also displays the direction in which the catheter tip is pointing, thus further assisting accurate catheter placement. The TLS further assists the clinician in determining when a malposition of the catheter tip has occurred, such as in the case where the tip has deviated from a desired venous path into another vein.

As disclosed herein, in an embodiment the system 10 can include additional functionality wherein determination of the proximity of the catheter distal tip 76A relative to a sino-atrial ("SA") or other electrical impulse-emitting node of the heart of the patient 70 can be determined, thus providing enhanced ability to accurately place the catheter distal tip in a desired location proximate the node. Also referred to herein as "ECG" or "ECG-based tip confirmation," this third modality of the system 10 enables detection of ECG signals from the SA node in order to place the catheter distal tip in a desired location within the patient vasculature. Note that the US, TLS, and ECG modalities are seamlessly combined in the present system 10 and can be employed in concert or individually to assist in catheter placement. Further details regarding the catheter placement system described herein can be found in U.S. Pat. No. 8,388,541, titled "Integrated System for Intravascular Placement of a Catheter," which is incorporated herein by reference in its entirety.

In reference to FIGS. 4C-7C, in an embodiment, the ultrasound ("US") portion of the system 10 further includes additional imaging functionality to enable an enhanced subcutaneous view of the patient body to be achieved. The additional imaging functionality is provided by an emitter 214, detector 216 and console 20. The emitter 214 is included with a needle 210 that is employed to gain access to a vein or other subcutaneous vessel or body portion. As shown in FIGS. 5A-5C as the needle 210/emitter 214 penetrates the skin surface and vasculature 222, different tissue types are illuminated as they respond differently to the light provided by the emitter 214.

In an embodiment, the emitter 214 is included at a distal end of a stylet 212 that is removably received within the lumen defined by the needle 210. The emitter 214 is positioned so as to be disposed at the distal end of the needle 210, and is configured to emit a light signal of a predetermined wavelength or wavelength range. In embodiments, the emitter 214 can be included as a component on the needle 210 itself, or on another component to be inserted into the patient such as a catheter, guidewire, or the like. It will be appreciated that one or more additional devices such as catheters, guidewires, introducers, and the like can also be disposed within the lumen of the needle 210.

In an embodiment, the stylet 212 includes a fiber optic cable that extends the length of the stylet 212 to the emitter 214 disposed at a distal end thereof. A light source 230 can be disposed proximally of the emitter 214 and generate a source of light including a given wavelength or range of wavelengths. The light can then be communicated to the emitter 214 by the fiber optic cable. In an embodiment, the light source 230 can be a Light Emitting Diode (LED), tungsten bulb, fluorescent bulb, or similar suitable light source capable of emitting a desired wavelength or range of wavelengths.

In an embodiment, the light source 230 is part of the emitter 214 and are both disposed at a distal end of the stylet 212 as a single unit. A cable can extend proximally from the emitter 214 to a power source. In an embodiment, the power source is a battery, mains power, or similar suitable power source, or combinations thereof.

As shown in FIG. 3A, a light detector 216 can be included with the probe 40 and positioned proximate the head 80 of the probe. It will be appreciated that the light detector 216 can also be included with another component or as a standalone configuration device. The detector 216 is configured to detect light emitted by the emitter 214 after the needle 210 has been inserted subcutaneously into the patient 70. In an embodiment, the system 10 includes an array of detectors 216, one or more of which can be included with the probe 40.

Figure 8A:
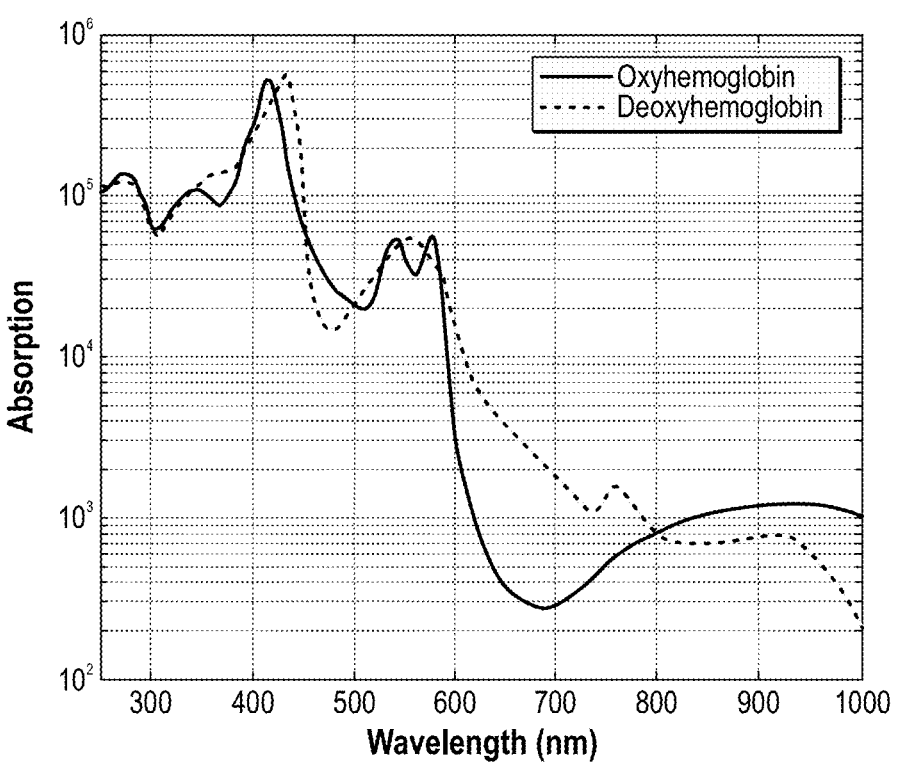
FIGS. 8A-8B show exemplary absorption spectra for different tissue components, according to embodiments disclosed herein.
Figure 8B:
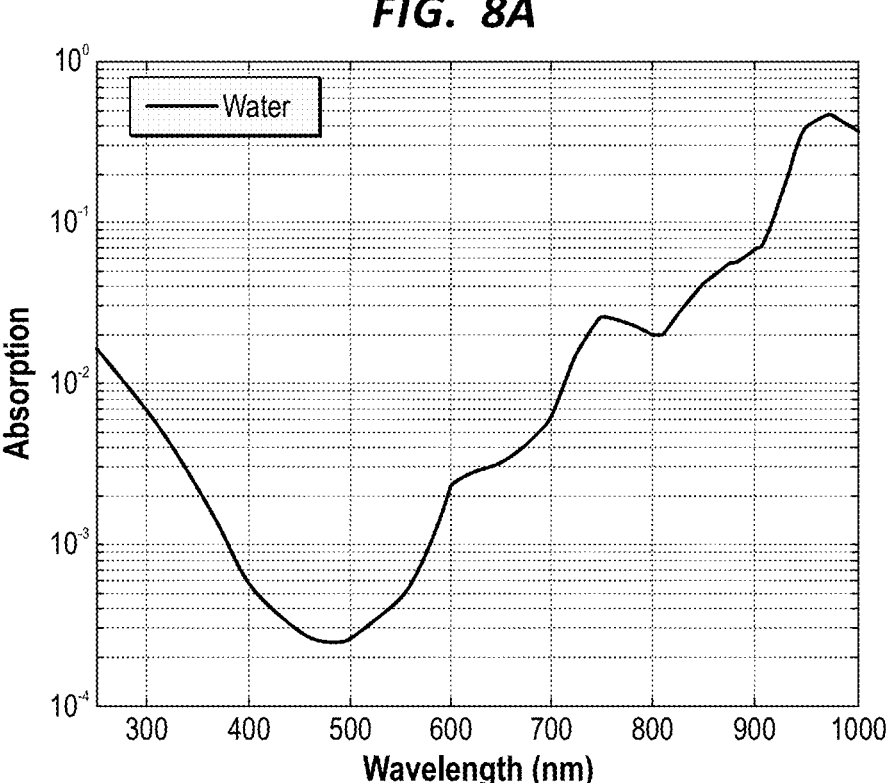

In an embodiment, the emitter 214 is configured to emit light within the infrared wavelength range. In an embodiment, the emitter 214 is configured to emit light within the near-infrared range including wavelengths from about 780 nm to about 3000 nm, which is an optical window for biological tissue. Light in the foregoing optical window, is capable of penetrating biological tissue more deeply than light outside the foregoing range of wavelengths. The infrared light penetrating and reflecting off of the tissue provide differing spectra of absorption coefficients depending on the different tissue components included in the tissue. Exemplary tissue components include oxyhemoglobin, deoxyhemoglobin, water, melanin, fat, etc., each of which show different profiles of absorption peaks across the infrared range. Exemplary absorption spectra are shown in FIGS. 8A-8B, where FIG. 8A shows the absorption spectra for both Oxyhemoglobin and Deoxyhemoglobin and FIG. 8B shows an absorption spectra for water. Accordingly, different tissue types, which include differing proportions of these tissue components, provide signature absorption spectra that can be detected and interpreted.

Figures 5A, 5B, 5C:
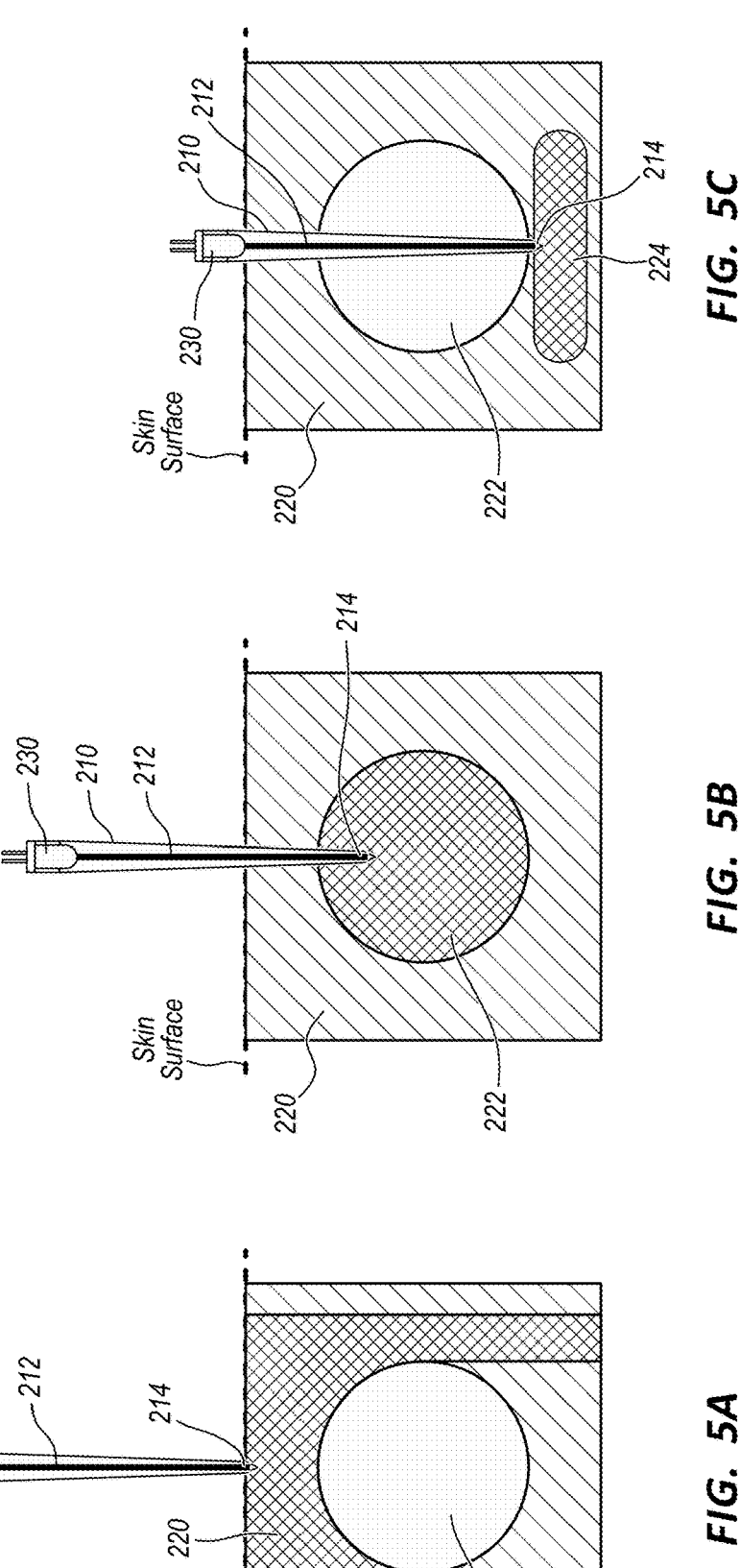
FIGS. 5A-5C show various front-end views of enhanced ultrasound images produced by the integrated system of FIG. 1 according to embodiments disclosed herein.

For example, as shown in FIGS. 5A-5C, the subcutaneous tissue 220, between the skin surface and the vessel will have different proportion of blood, water, melanin, fat, etc. than that of the vessel wall, vessel 222, and deeper tissues 224 below the vessel 222. As such, the light from the emitter 214 is reflected differently from these different tissue types, which can be detected and interpreted by the detector 216. Moreover, the vessel being accessed can be identified as arterial or venous depending on the proportion of oxyhemoglobin and deoxyhemoglobin detected. In addition, the boundary layer between two different tissue types provides a difference in impedance which can reflect a portion of the light back into the tissue. As such, the emitter 214 disposed within different tissue structures 220, 222, 224, illuminates the structures and highlights the boundaries between the structures. Detecting and interpreting the wavelength profiles of the reflected light can provide information regarding the location of the emitter. This light-based information can be superimposed on an ultrasound image of the vessel to facilitate first-stick access of patient vasculature.

Figure 4C:
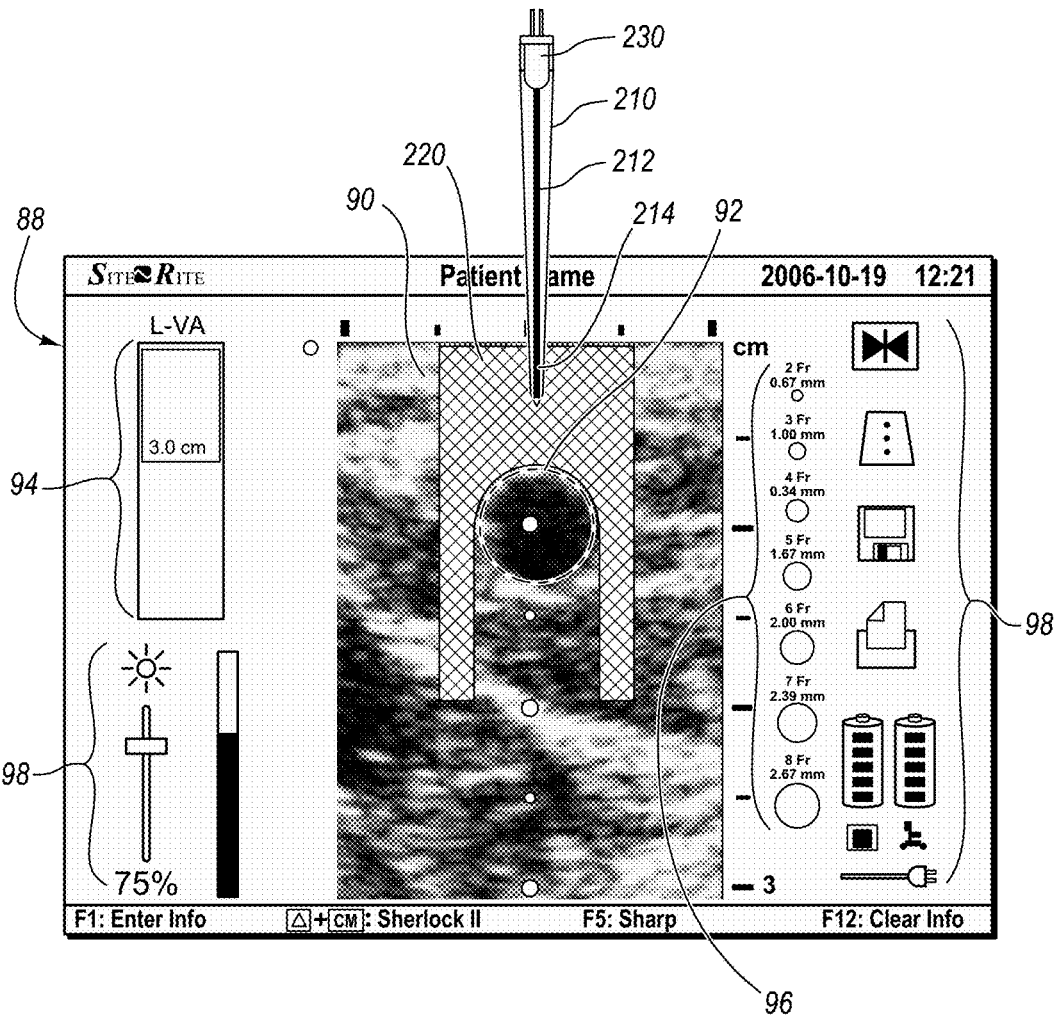
FIG. 4C is a screenshot of an enhanced ultrasound image as depicted on a display of the integrated system of FIG. 1.

As shown in FIG. 4C, the processor 22 of the system 10 can process the light-based information, sensed by the detector 216, and combine them with the ultrasound imaging data acquired by the ultrasound probe 40 to produce an enhanced image. Further examples of enhanced images are shown in FIGS. 5A-7C, together with the needle 210, stylet 212, and the emitter 214. FIGS. 5A-5CA show a front end view of subcutaneous tissue and a vessel 222 to be accessed. As shown in FIG. 5A, as the needle 210 penetrates the skin surface of the patient, light from the emitter 214 penetrates and illuminates subcutaneous body tissue 220 surrounding a target vessel 222. As shown in FIG. 5B, once the needle 210 has penetrated the vessel 222, light emitted from the emitter 214 illuminates the vessel interior instead of the body tissue surrounding the vein. Should the needle 210 extend completely through the vein 222, the emitter 214 will illuminate the tissue 224 disposed below the vessel 222, as seen in FIG. 5C.

Visualization of these different needle distal tip positions of FIGS. 5A-5C can be superimposed atop the traditional ultrasound image, for example, as shown in FIG. 4C. This provides an enhanced ultrasound/infrared image of the vessel and the position of the distal tip of the needle 210 relative thereto, depicted on the display 30 (or other suitable output device). In turn, this will assist the clinician in determining when the distal tip of the needle 210 is desirably disposed within the lumen of the vessel 222 or other body portion. It will be appreciated that the system 10 can provide various differently angled views of the enhanced image, including a transverse, front-end view (FIGS. 5A-5C), a longitudinal, side-profile view (FIGS. 6A-6C), a top-down, plan-view, ((FIGS. 7A-7C), a three-dimensionally rendered image, or combinations thereof.

Figures 6A, 6B, 6C:
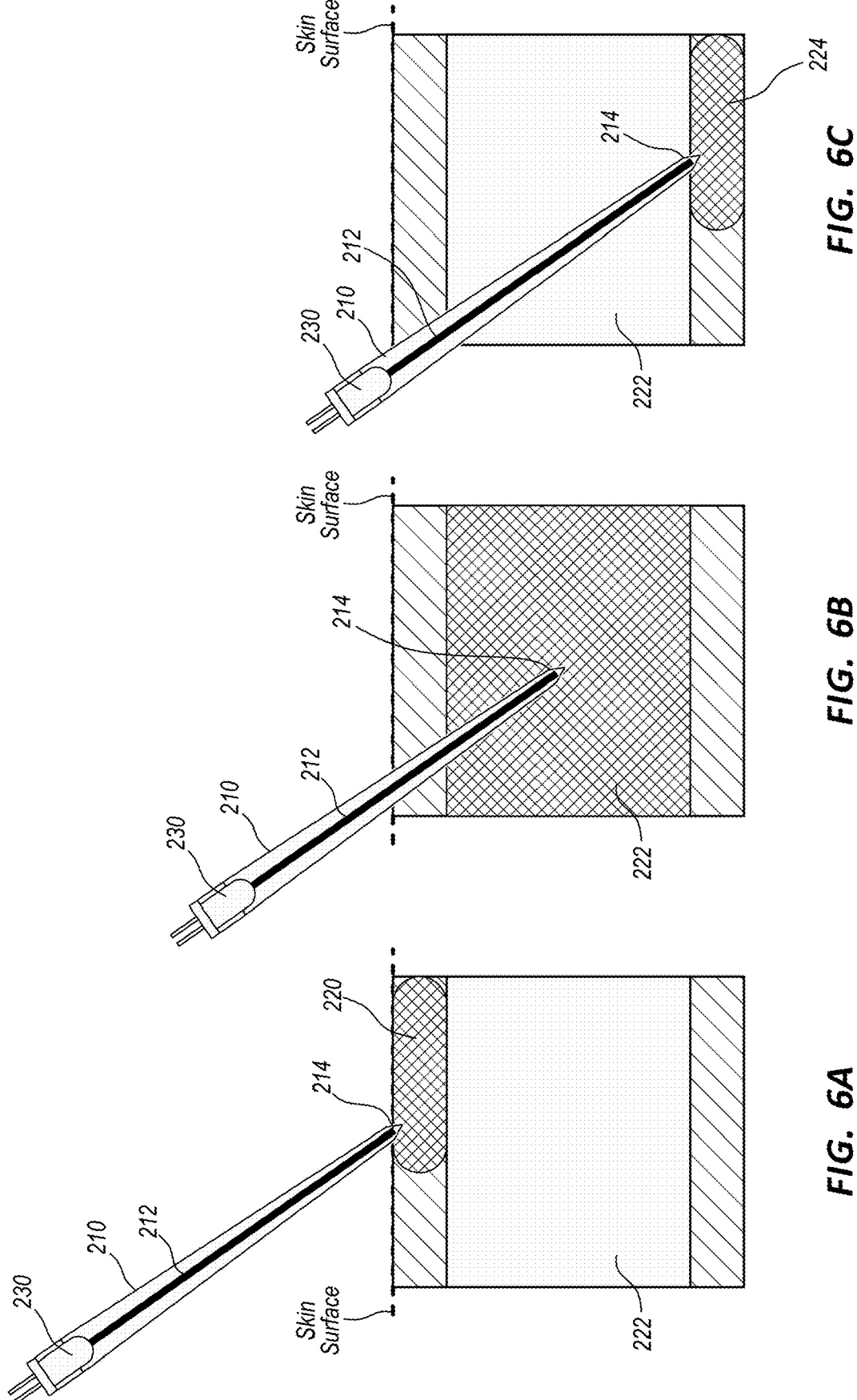
FIGS. 6A-6C show various side profile views of enhanced ultrasound images produced by the integrated system of FIG. 1 according to embodiments disclosed herein.

FIGS. 6A-6C show an enhanced side-view US-images during the insertion of the needle 210, both prior to insertion of the needle 210 into the vessel 222 (FIG. 6A), accessing the vessel 222 (FIG. 6B), and where the needle 210 has breached the far side of the vessel 222 (FIG. 6C). FIG. 6A shows an enhanced side-view image where the tip of the needle 210, including the emitter 214, is at or within the subcutaneous tissue 220 that is above the vessel 222. These tissues surrounding the vessel 220 are illuminated while the vessel 222 itself remains unilluminated due to the attenuation of the light at the wall of the vessel.

FIG. 6B shows an enhanced side-view image where the tip of the needle 210, and the emitter 214, has passed through the vessel wall and entered the vessel 222. The vessel 220 itself is now illuminated while the tissues surrounding the vessel 222 remain unilluminated. FIG. 6C shows an enhanced side-view image where the tip of the needle 210, including the emitter 214, has passed through the vessel wall on a far side, breaching the vessel and entering the tissues below the vessel 222. The tissues below the vessel 222 are now illuminated while the vessel 222 itself is now unilluminated.

Figures 7A, 7B, 7C:
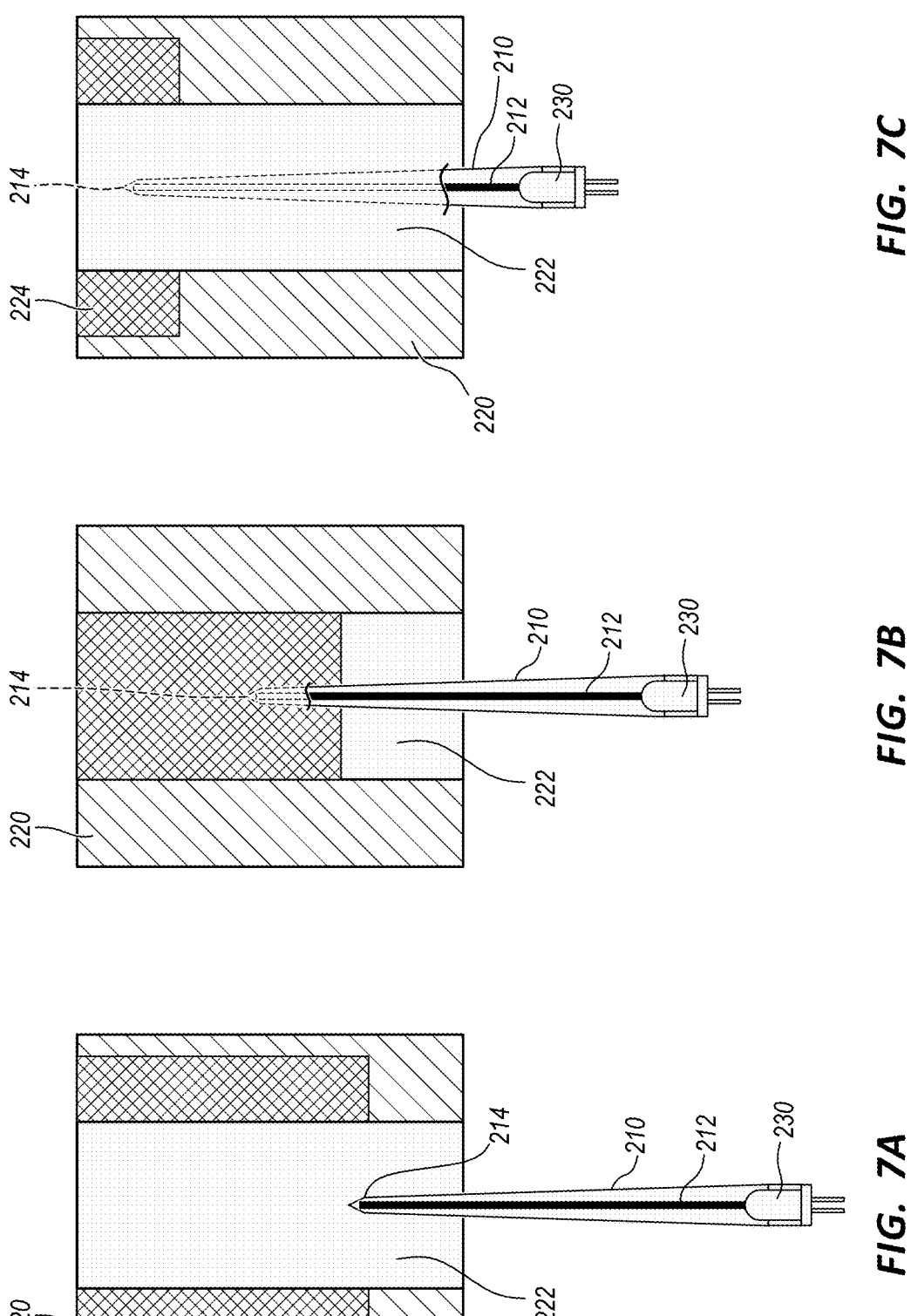
FIGS. 7A-7C show various plan views of enhanced ultrasound images produced by the integrated system of FIG. 1 according to embodiments disclosed herein.

FIGS. 7A-7C show a plan-view of enhanced US-images during the insertion of the needle 210, both prior to insertion of the vessel 222 (FIG. 7A), accessing the vessel 222 (FIG. 7B), and where the needle 210 has breached the far side of the vessel 222 (FIG. 7C). FIG. 7A shows an enhanced image where the tip of the needle 210 including the emitter 214 is at or within the subcutaneous tissue that is above the vessel 222. The tissues surrounding the vessel 220 are illuminated while the vessel 222 itself remains unilluminated. Advantageously, this highlights the boundaries of the vessel 222 which helps guide the position of the needle to a mid-point of the vessel 222.

FIG. 7B shows an enhanced side-view image where the tip of the needle 210, and the emitter 214, has passed through the vessel wall and entered the vessel 222. The vessel 220 itself is now illuminated while the tissues surrounding the vessel 222 remain unilluminated. FIG. 7C shows an enhanced side-view image where the tip of the needle 210, including the emitter 214, has passed through the vessel wall on a far side, breaching the vessel and entering the tissues below the vessel 222. The tissues below the vessel 222 are now illuminated while the vessel 222 itself is now unilluminated.

In an embodiment, as described herein, the detector 216 can determine differences between arterial and venous vasculature based on the profile of absorbance spectra of reflected light. The wavelengths provided by the emitter 214, and the wavelengths received by the detector 216 can be compared and identified as either "red-shifted" or "blue-shifted" to determine if the vessel 222 being accessed is arterial or venous, respectively. The system 10 can then indicate these differences either on the display 30 or by various visual, auditory, or tactile alerts as described herein.

In an embodiment, the light detector 216 and console 20 can detect and reproduce the illuminated portions on the display 30 and superimpose these images onto the US image of the same area. In an embodiment, the detector 216 can detect more subtle differences in reflected or absorbed light that would otherwise be indeterminable by the human eye. Accordingly, the detector 216 can detect and interpret the light-based information, and reproduce these data as enhanced images on the display 30. In addition, the system 10 can provide various visual, auditory, and/or tactile alerts, as the position of the needle tip/emitter 214 moves, relative to the vessel 222.

For example, the display 30 can provide an image of the needle relative to the vessel. Once the needle tip has entered the vessel 222, the display can provide an alert, such as green tick. If the needle 210 is advanced too far and breaches the far side of the vessel, entering the tissues 224, an auditory alert, or a tactile vibration can indicate to the user that the needle 210 has been advanced too far. Auditory and tactile alerts advantageously notify the user without the user needing to observe the display 30.

Embodiments of the invention may be embodied in other specific forms without departing from the spirit of the present disclosure. The described embodiments are to be considered in all respects only as illustrative, not restrictive. The scope of the embodiments is, therefore, indicated by the appended claims rather than by the foregoing description. All changes that come within the meaning and range of equivalency of the claims are to be embraced within their scope.

What is claimed:

1. An imaging system, comprising:

an ultrasound probe for producing and receiving ultrasound signals from a patient, the ultrasound probe including:

a head configured for placement against skin of the patient; and control buttons together with a button-and-memory controller to control imaging functionality of the imaging system including enhanced imaging functionality with biological tissue-penetrating infrared light, the control buttons precluding any need for a clinician to reach out of a sterile field in order to control the imaging functionality;

an emitter configured for emitting at least the biological tissue-penetrating infrared light into a biological tissue of the patient, the emitter disposed in a distal tip of a needle;

a light detector in a distal portion of the ultrasound probe configured to detect any infrared light illuminating structures and boundaries between the infrared light illuminating structures within the biological tissue; and a display configured to provide an ultrasound image including a position of the distal tip of the needle superimposed thereover in accordance with ultrasound information from the ultrasound probe and light-based information from the light detector for facilitating first-stick vascular access of the patient with the needle through visualization of the needle on the ultrasound image as it is inserted into a vessel of the biological tissue to gain the first-stick vascular access.

2. The system according to claim 1, wherein the emitter is configured to emit the biological tissue-penetrating infrared light within a range of wavelengths between 780 nm and 3000 nm.

3. The system according to claim 1, wherein the emitter includes a light source configured to produce the biological tissue-penetrating infrared light.

4. The system according to claim 1, further including a light source configured to produce the biological tissue-penetrating infrared light and a fiber optic cable distally extending from the light source configured to communicate the biological tissue-penetrating infrared light between the light source and the emitter.

5. The system according to claim 1, wherein the ultrasound image is enhanced with the light-based information from the light detector in accordance with whether the biological tissue-penetrating infrared light illuminates the biological tissue above the vessel, within the vessel, or below the vessel.

6. The system according to claim 5, wherein illumination of the biological tissue above the vessel but not the vessel itself indicates the vessel has not been penetrated by the needle, illumination of the biological tissue within the vessel but not the biological tissue around the vessel indicates the needle has penetrated and is disposed within the vessel, and illumination of the biological tissue below the vessel but not the vessel itself indicates the needle has passed completely through the vessel.

7. The system according to claim 1, wherein the ultrasound image is enhanced with the light-based information from the light detector in accordance with absorption spectra of the biological tissue, the absorption spectra having absorption peaks indicative of various tissue components.

8. The system according to claim 7, wherein a processor in a console of the imaging system determines that the vessel being accessed is arterial or venous in accordance with a proportion of oxyhemoglobin and deoxyhemoglobin detected in the absorption spectra by way of the absorption peaks for oxyhemoglobin and deoxyhemoglobin.

9. The system according to claim 1, wherein the emitter is incorporated into a distal end of a stylet, which, in turn, is disposed within a lumen of the needle.

10. The system according to claim 1, wherein the emitter is incorporated into the distal tip of the needle.

11. The system according to claim 1, wherein the display is further configured to depict the needle relative to the vessel in accordance with the ultrasound image, thereby assisting the clinician in determining when the distal tip of the needle is disposed within the vessel.

* * * * *